US012409073B2

(12) United States Patent
Drake

(10) Patent No.: US 12,409,073 B2
(45) Date of Patent: Sep. 9, 2025

(54) HEMOSTATIC TRAUMA PACK AND METHOD FOR APPLYING THE PACK TO WOUNDS

(71) Applicant: James Drake, Minnespolis, MN (US)

(72) Inventor: James Drake, Minnespolis, MN (US)

(*) Notice: Subject to any disclaimer, the term of this patent is extended or adjusted under 35 U.S.C. 154(b) by 419 days.

(21) Appl. No.: 18/102,742

(22) Filed: Jan. 29, 2023

(65) Prior Publication Data
US 2024/0252359 A1    Aug. 1, 2024

(51) Int. Cl.
*A61F 13/0206*    (2024.01)
*A61F 13/00*    (2024.01)

(52) U.S. Cl.
CPC  *A61F 13/0206* (2013.01); *A61F 2013/00106* (2013.01)

(58) Field of Classification Search
CPC .......... A61F 11/12; A61F 11/14; A61F 13/00; A61F 13/00051; A61F 13/00055; A61F 13/00059; A61F 13/00063; A61F 13/00072; A61F 13/00076; A61F 13/0008; A61F 13/00085; A61F 13/00987; A61F 13/00991; A61F 13/00995; A61F 13/01; A61F 13/01008; A61F 13/01012; A61F 13/01017; A61F 13/01021; A61F 13/01025; A61F 13/01029; A61F 13/01034; A61F 13/01038; A61F 13/01042; A61F 13/01046; A61F 13/02; A61F 13/0203; A61F 13/0206; A61F 13/0209; A61F 13/0213; A61F 13/022; A61F 13/0223; A61F 13/0226;

(Continued)

(56) References Cited

U.S. PATENT DOCUMENTS 3,653,502 A * 4/1972 Beaudoin .............. A61F 15/001
                                                     206/440
4,334,530 A * 6/1982 Hassell .............. A61F 13/0203
                                                     602/42

(Continued)

FOREIGN PATENT DOCUMENTS

CA       2486654    * 12/2003    ........... A61K 9/7084
CA       2486654 A1 * 12/2003    ........... A61K 9/7084

(Continued)

*Primary Examiner* — Anthony D Stashick
*Assistant Examiner* — Marcos Javier Rodriguez Molina
(74) *Attorney, Agent, or Firm* — MARK A. LITMAN & ASSOCIATES, P.A.

(57) ABSTRACT

A device delivers a sterile hemostasis material to wounds with:
- a packet comprising a non-porous surface with an pocket and a surrounding edge structure, the packet having a leading edge and a rearward edge;
- within the packet is a sterile hemostatic mass capable of clotting mammalian blood when it contacts mammalian blood;
- a bottom layer attached to the surrounding edge structure secures the sterile hemostatic mass within the packet, said bottom layer having a first end and a second end corresponding to the leading edge and the rearward edge of the packet; and
- a lower structural element below the bottom layer is adhered to at least the first end of the bottom layer such that when the lower structural element is progressively pulled parallel to the surrounding edge structure, the first end of the bottom layer is progressively separated from the surrounding edge structure, exposing sterile hemostatic mass exposed.

19 Claims, 4 Drawing Sheets

(58) Field of Classification Search
CPC ................ A61F 13/023; A61F 13/0233; A61F
13/0236; A61F 13/024; A61F 13/0243;
A61F 13/0246; A61F 13/025; A61F
13/0253; A61F 13/0256; A61F 13/0259;
A61F 13/0263; A61F 13/0266; A61F
13/0269; A61F 13/0273; A61F 13/0276;
A61F 13/0279; A61F 13/0283; A61F
13/0286; A61F 13/0289; A61F 13/04;
A61F 13/041; A61F 13/043; A61F
13/045; A61F 13/046; A61F 13/05; A61F
13/06; A61F 13/061; A61F 13/062; A61F
13/064; A61F 13/065; A61F 13/066;
A61F 13/067; A61F 13/068; A61F
13/069; A61F 13/08; A61F 13/085; A61F
13/10; A61F 13/101; A61F 13/102; A61F
13/104; A61F 13/105; A61F 13/107;
A61F 13/108; A61F 13/12; A61F 13/122;
A61F 13/124; A61F 13/126; A61F
13/128; A61F 13/14; A61F 13/141; A61F
13/143; A61F 13/145; A61F 13/146;
A61F 13/148; A61F 13/15; A61F
13/15203; A61F 13/15268; A61F
13/15577; A61F 13/15585; A61F
13/15634; A61F 13/15658; A61F
13/15666; A61F 13/15699; A61F
13/15731; A61F 13/15764; A61F
13/15772; A61F 13/15804; A61F 13/20;
A61F 13/2002; A61F 13/2005; A61F
13/2011; A61F 13/2022; A61F 13/2042;
A61F 13/2051; A61F 13/2057; A61F
13/2082; A61F 13/2085; A61F 13/36;
A61F 13/38; A61F 13/385; A61F 13/42;
A61F 13/44; A61F 13/45; A61F 13/471;
A61F 13/47218; A61F 13/47227; A61F
13/47254; A61F 13/47263; A61F
13/4752; A61F 13/4756; A61F 13/476;
A61F 13/49; A61F 13/49006; A61F
13/49014; A61F 13/49017; A61F
13/4902; A61F 13/49061; A61F 13/494;
A61F 13/495; A61F 13/496; A61F
13/4963; A61F 13/505; A61F 13/511;
A61F 13/51104; A61F 13/51108; A61F
13/51305; A61F 13/514; A61F 13/51401;
A61F 13/51405; A61F 13/51476; A61F
13/53; A61F 13/531; A61F 13/532; A61F
13/5323; A61F 13/534; A61F 13/53409;
A61F 13/53436; A61F 13/535; A61F
13/536; A61F 13/537; A61F 13/53708;
A61F 13/53713; A61F 13/53717; A61F
13/53743; A61F 13/53747; A61F
13/53756; A61F 13/5376; A61F 13/538;
A61F 13/539; A61F 13/551; A61F
13/5514; A61F 13/55145; A61F 13/5515;
A61F 13/55175; A61F 13/55185; A61F
13/56; A61F 13/5611; A61F 13/5616;
A61F 13/565; A61F 13/58; A61F 13/581;
A61F 13/60; A61F 13/62; A61F 13/622;
A61F 13/64; A61F 13/82; A61F 13/84;
A61F 13/8405; A61F 15/00; A61F
15/001; A61F 15/002; A61F 15/003;
A61F 15/004; A61F 15/005; A61F
15/006; A61F 15/007; A61F 15/008;
A61F 15/02; A61F 17/00; A61F 2/00;
A61F 2/0045; A61F 2/005; A61F 2/0059;
A61F 2/0063; A61F 2/0077; A61F 2/02;
A61F 2/0811; A61F 2/2803; A61F
2/30907; A61F 2/3859; A61F 2/3872;
A61F 2/389; A61F 2/442; A61F 2/50;
A61F 2/5046; A61F 2/54; A61F 2/583;
A61F 2/585; A61F 2/586; A61F 2/60;
A61F 2/605; A61F 2/642; A61F 2/70;
A61F 2/72; A61F 2/76; A61F 2/78; A61F
2002/0068; A61F 2002/2807; A61F
2002/5001; A61F 2002/5007; A61F
2002/5016; A61F 2002/5026; A61F
2002/5072; A61F 2002/587; A61F
2002/6836; A61F 2002/6845; A61F
2002/701; A61F 2002/704; A61F
2002/7625; A61F 2002/7635; A61F
2002/7695; A61F 2002/7862; A61F
2005/0016; A61F 2005/002; A61F
2005/0132; A61F 2005/0134; A61F
2005/0137; A61F 2005/0144; A61F
2005/0155; A61F 2005/0158; A61F
2005/0165; A61F 2005/0169; A61F
2005/0172; A61F 2005/0174; A61F
2005/0176; A61F 2005/0179; A61F
2005/0181; A61F 2005/0183; A61F
2005/0186; A61F 2005/0188; A61F
2005/0197; A61F 2005/4402; A61F
2005/4415; A61F 2007/0001; A61F
2007/0002; A61F 2007/0003; A61F
2007/0004; A61F 2007/0008; A61F
2007/0009; A61F 2007/0017; A61F
2007/0022; A61F 2007/0024; A61F
2007/0027; A61F 2007/0029; A61F
2007/003; A61F 2007/0034; A61F
2007/0035; A61F 2007/0036; A61F
2007/0037; A61F 2007/0038; A61F
2007/0039; A61F 2007/004; A61F
2007/0041; A61F 2007/0042; A61F
2007/0044; A61F 2007/0045; A61F
2007/0046; A61F 2007/005; A61F
2007/0052; A61F 2007/0054; A61F
2007/0055; A61F 2007/0057; A61F
2007/0059; A61F 2007/006; A61F
2007/0062; A61F 2007/0063; A61F
2007/0064; A61F 2007/0068; A61F
2007/0069; A61F 2007/0071; A61F
2007/0073; A61F 2007/0075; A61F
2007/0078; A61F 2007/0086; A61F
2007/0088; A61F 2007/0091; A61F
2007/0093; A61F 2007/0094; A61F
2007/0095; A61F 2007/0096; A61F
2007/0098; A61F 2007/0211; A61F
2007/0214; A61F 2007/0219; A61F
2007/022; A61F 2007/0222; A61F
2007/0225; A61F 2007/0226; A61F
2007/0228; A61F 2007/023; A61F
2007/0231; A61F 2007/0238; A61F
2007/0239; A61F 2007/0244; A61F
2007/0247; A61F 2007/0249; A61F
2007/0252; A61F 2007/0253; A61F
2007/0258; A61F 2007/026; A61F
2007/0261; A61F 2007/0263; A61F
2007/0268; A61F 2007/0276; A61F
2007/0279; A61F 2007/0285; A61F
2007/0292; A61F 2007/0293; A61F
2007/0296; A61F 2007/101; A61F 2007/105; A61F 2007/108; A61F
2013/00089; A61F 2013/00093; A61F
2013/00097; A61F 2013/00102; A61F
2013/00106; A61F 2013/00119; A61F
2013/00123; A61F 2013/00127; A61F
2013/00131; A61F 2013/00136; A61F
2013/00148; A61F 2013/00153; A61F
2013/00157; A61F 2013/00165; A61F
2013/0017; A61F 2013/00174; A61F
2013/00182; A61F 2013/00187; A61F
2013/00204; A61F 2013/00212; A61F
2013/00217; A61F 2013/00221; A61F
2013/00225; A61F 2013/00229; A61F
2013/00234; A61F 2013/00238; A61F
2013/00246; A61F 2013/00251; A61F
2013/00255; A61F 2013/00259; A61F
2013/00263; A61F 2013/00268; A61F
2013/00272; A61F 2013/0028; A61F
2013/00285; A61F 2013/00289; A61F
2013/00293; A61F 2013/00302; A61F
2013/00314; A61F 2013/00319; A61F
2013/00323; A61F 2013/00327; A61F
2013/00353; A61F 2013/00357; A61F
2013/00361; A61F 2013/0037; A61F
2013/00374; A61F 2013/00382; A61F
2013/00387; A61F 2013/00395; A61F
2013/004; A61F 2013/00404; A61F
2013/00412; A61F 2013/00421; A61F
2013/00429; A61F 2013/00451; A61F
2013/00463; A61F 2013/00476; A61F
2013/0048; A61F 2013/00497; A61F
2013/00502; A61F 2013/00527; A61F
2013/00531; A61F 2013/0054; A61F
2013/00544; A61F 2013/00557; A61F
2013/00561; A61F 2013/0057; A61F
2013/00574; A61F 2013/00587; A61F
2013/00591; A61F 2013/006; A61F
2013/00604; A61F 2013/00617; A61F
2013/00621; A61F 2013/00629; A61F
2013/00634; A61F 2013/00646; A61F
2013/00651; A61F 2013/00659; A61F
2013/00663; A61F 2013/00702; A61F
2013/0071; A61F 2013/00727; A61F
2013/00731; A61F 2013/00748; A61F
2013/00753; A61F 2013/00761; A61F
2013/00765; A61F 2013/00782; A61F
2013/00795; A61F 2013/00804; A61F
2013/00808; A61F 2013/00821; A61F
2013/00825; A61F 2013/00834; A61F
2013/00838; A61F 2013/00851; A61F
2013/00855; A61F 2013/00863; A61F
2013/00868; A61F 2013/00889; A61F
2013/00897; A61F 2013/00906; A61F
2013/0091; A61F 2013/00927; A61F
2013/00931; A61F 2013/0094; A61F
2013/00944; A61F 2013/00957; A61F
2013/00961; A61F 2013/00974; A61M
1/0209; A61M 1/0281; A61M 1/029;
A61M 1/04; A61M 1/34; A61M 1/341;
A61M 1/3486; A61M 1/3618; A61M
1/3621; A61M 1/3659; A61M 1/3666;
A61M 1/3693; A61M 1/3695; A61M
1/67; A61M 1/68; A61M 1/682; A61M
1/732; A61M 1/734; A61M 1/74; A61M
1/77; A61M 1/772; A61M 1/78; A61M
1/80; A61M 1/81; A61M 1/85; A61M
1/86; A61M 1/89; A61M 1/912; A61M
1/913; A61M 1/915; A61M 1/94; A61M
1/95; A61M 1/96; A61M 1/966; A61M
1/98; A61M 1/982; A61M 11/005; A61M
11/042; A61M 15/009; A61M 15/02;
A61M 15/0463; A61M 16/06; A61M
16/0816; A61M 19/00; A61M 2005/005;
A61M 2005/1586; A61M 2005/1588;
A61M 2005/3139; A61M 2005/3142;
A61M 2025/0004; A61M 2025/0031;
A61M 2025/0056; A61M 2025/0063;
A61M 2025/0096; A61M 2025/015;
A61M 2025/0183; A61M 2025/0233;
A61M 2025/028; A61M 2025/0286;
A61M 2025/105; A61M 2025/1052;
A61M 2025/1081; A61M 2025/1086;
A61M 2025/0007; A61M 2037/0023;
A61M 2037/0053; A61M 2037/0061;
A61M 2039/0258; A61M 2039/0279;
A61M 2039/0282; A61M 2039/1083;
A61M 2039/229; A61M 2039/0007;
A61M 2202/0208; A61M 2202/0415;
A61M 2202/0427; A61M 2202/047;
A61M 2202/064; A61M 2205/02; A61M
2205/0238; A61M 2205/0272; A61M
2205/0288; A61M 2205/054; A61M
2205/057; A61M 2205/078; A61M
2205/11; A61M 2205/19; A61M
2205/273; A61M 2205/3306; A61M
2205/331; A61M 2205/3327; A61M
2205/3331; A61M 2205/3344; A61M
2205/3348; A61M 2205/3368; A61M
2205/3379; A61M 2205/3523; A61M
2205/3553; A61M 2205/3584; A61M
2205/3653; A61M 2205/50; A61M
2205/502; A61M 2205/587; A61M
2205/75; A61M 2205/7545; A61M
2205/8206; A61M 2210/06; A61M
2210/0606; A61M 2210/1007; A61M
2210/1021; A61M 2210/1053; A61M
2210/1078; A61M 2210/1089; A61M
2210/125; A61M 2230/205; A61M
2230/42; A61M 2230/0012; A61M
25/002; A61M 25/0023; A61M 25/0041;
A61M 25/0043; A61M 25/0053; A61M
25/0054; A61M 25/0068; A61M 25/0074;
A61M 25/008; A61M 25/0097; A61M
25/01; A61M 25/0102; A61M 25/0125;
A61M 25/0136; A61M 25/0152; A61M
25/0155; A61M 25/0662; A61M 25/0668;
A61M 25/1002; A61M 25/1011; A61M
25/10182; A61M 25/10188; A61M
25/1025; A61M 25/104; A61M 27/00;
A61M 3/00; A61M 3/0202; A61M
3/0258; A61M 3/0262; A61M 31/00;
A61M 31/002; A61M 35/30; A61M
37/00; A61M 37/0076; A61M 37/0092;
A61M 39/00; A61M 39/06; A61M
39/0606; A61M 39/24; A61M 39/28;
A61M 5/14; A61M 5/1407; A61M
5/14244; A61M 5/14276; A61M 5/16813;
A61M 5/1723

USPC ... 206/5, 204, 205, 206, 207, 210, 216, 217,
206/219, 221, 222, 223, 229, 232, 278,
206/338, 339, 340, 341, 345, 363, 364,
206/365, 366, 370, 390, 395, 398, 399,
206/409, 411, 438, 440, 441, 447, 459.5,
206/460, 461, 469, 471, 476, 482, 484,
206/494, 497, 499, 519, 523, 524.1,
206/524.4, 524.6, 524.8, 528, 531, 532,
206/534, 54, 561, 563, 564, 568, 570,
206/571, 572, 575, 63.3, 63.5, 701, 756,
206/803, 812, 820, 822, 828; 220/500,
220/501, 503, 563, 564; 424/443, 446,
424/447, 448, 449; 428/34.1, 40.1;
602/48; 604/304, 307

See application file for complete search history.

(56) References Cited

U.S. PATENT DOCUMENTS

| | | | | |
|---|---|---|---|---|
| 5,099,832 A * | 3/1992 | Ward | ................... | A61F 15/001 |
| | | | | 602/41 |
| 7,506,760 B2 * | 3/2009 | Grossman | ............. | A61F 15/001 |
| | | | | 206/440 |
| 2003/0225354 A1 * | 12/2003 | Drake | .................. | A61K 9/7084 |
| | | | | 428/40.1 |
| 2004/0004014 A1 * | 1/2004 | Grossman | ............. | A61F 15/002 |
| | | | | 206/440 |
| 2004/0138602 A1 * | 7/2004 | Rossen | ............... | A61F 13/0226 |
| | | | | 602/41 |
| 2006/0155235 A1 * | 7/2006 | Sawyer | ............... | A61F 13/0203 |
| | | | | 602/48 |
| 2015/0136628 A1 * | 5/2015 | Bertelsen | ............... | A61B 50/00 |
| | | | | 206/440 |

FOREIGN PATENT DOCUMENTS

| | | | | |
|---|---|---|---|---|
| WO | WO-2010110130 | * | 9/2010 | ....... A61F 13/00076 |
| WO | WO-2010110130 A1 | * | 9/2010 | ....... A61F 13/00076 |

* cited by examiner

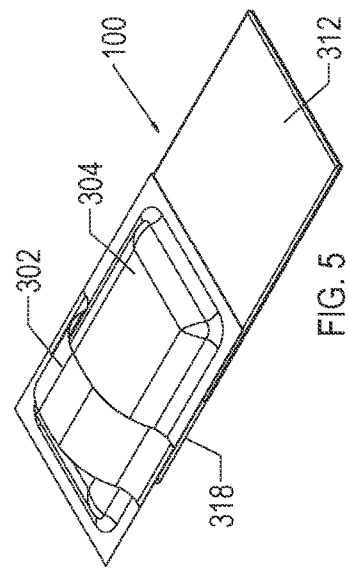
FIG. 1
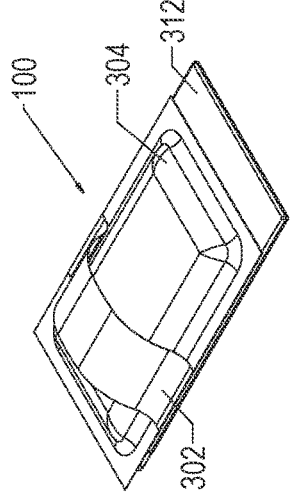
FIG. 4
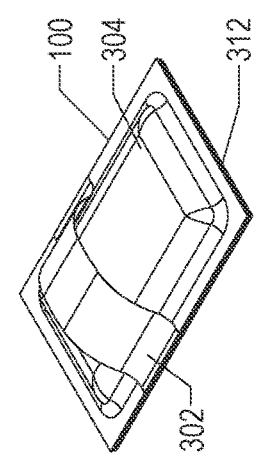
FIG. 5
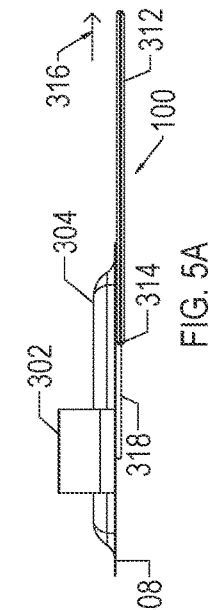
FIG. 2
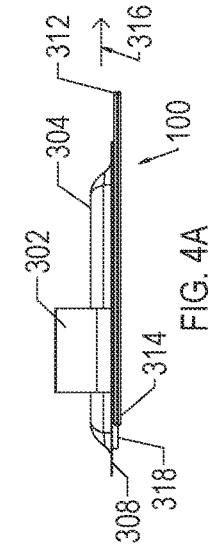
FIG. 4A
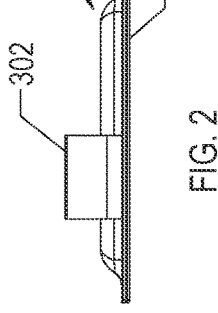
FIG. 5A
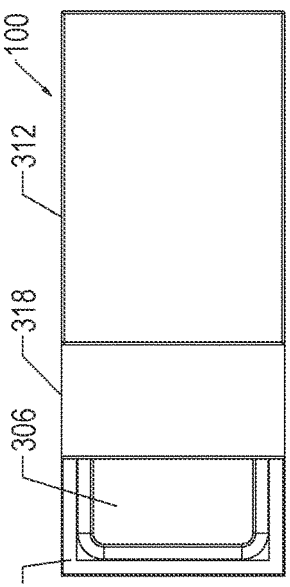
FIG. 2A
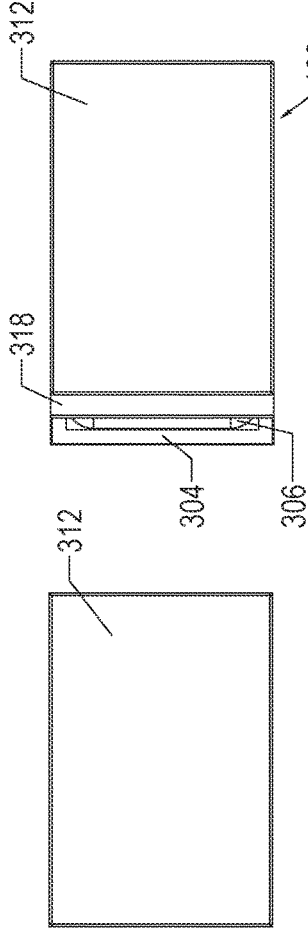
FIG. 4B
FIG. 5B

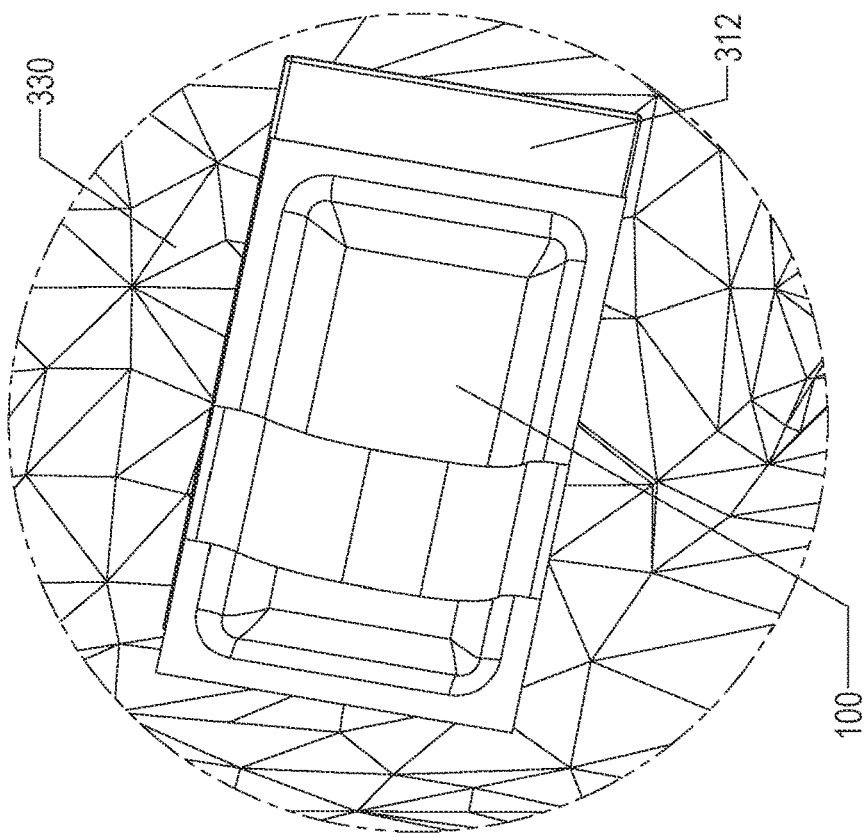
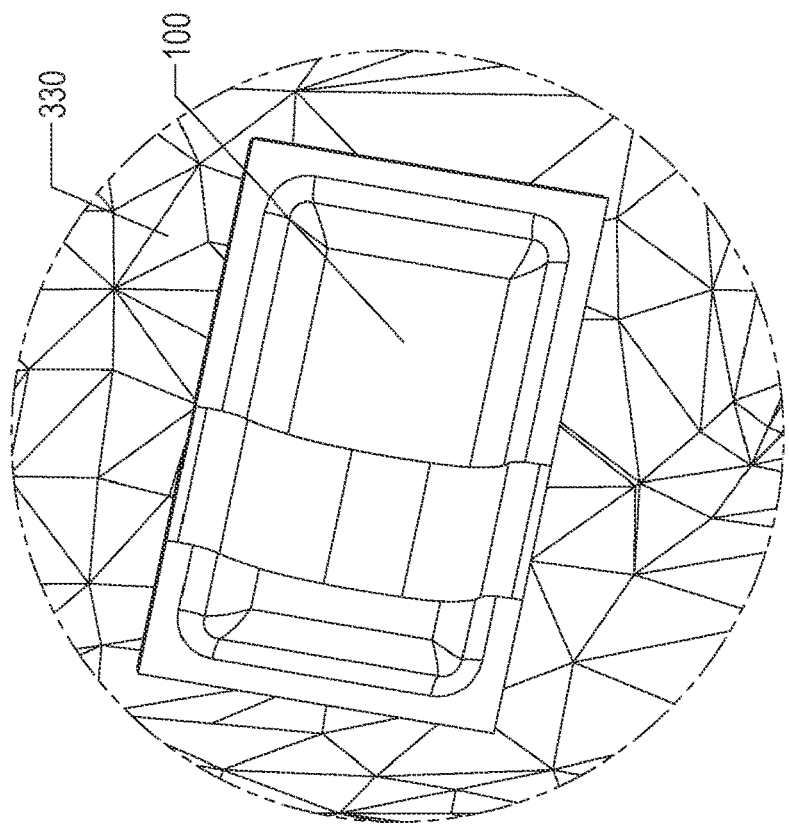

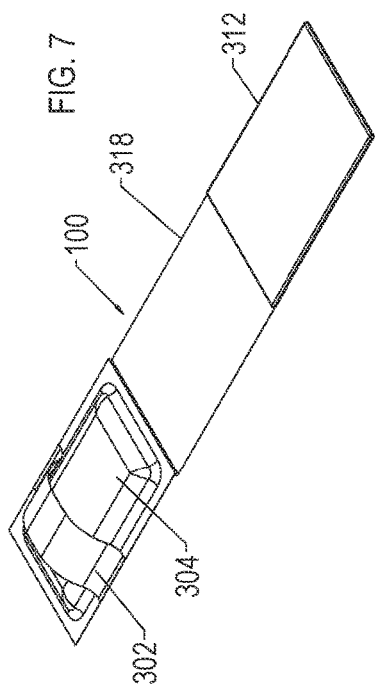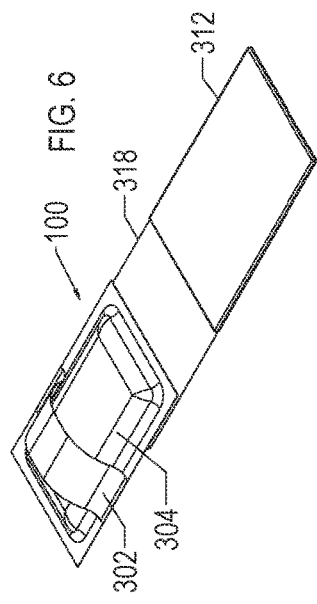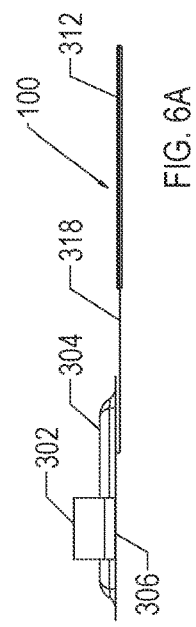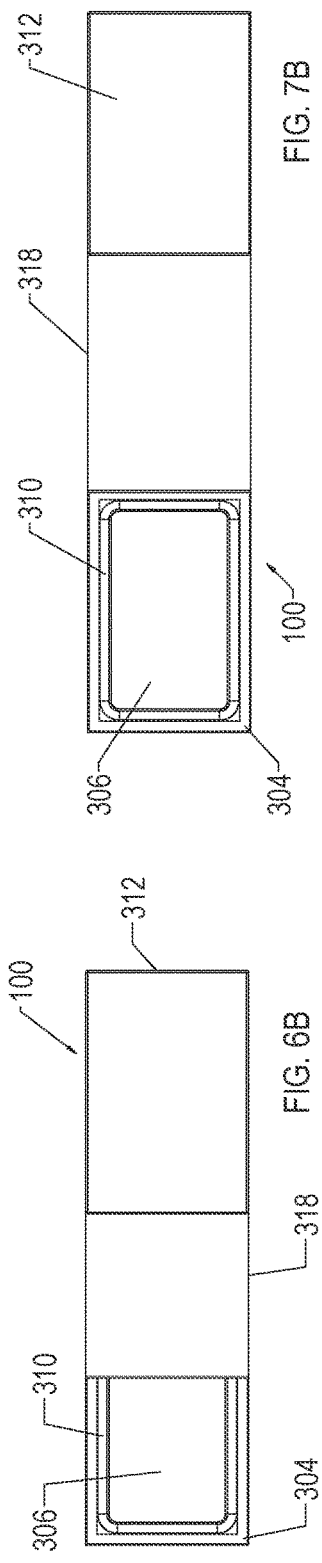

HEMOSTATIC TRAUMA PACK AND METHOD FOR APPLYING THE PACK TO WOUNDS

BACKGROUND OF THE INVENTION

1. Field of the Invention

The present invention relates to the field of treatment of traumatic wounds to the body, the use of hemostatic agents to treat such trauma wounds, and specific devices for applying hemostatic agents to wounds even as a field dressing system.

2. Background of the Art

External wounds and concomitant bleeding are the most common injuries suffered by animals. Scratches, cuts, abrasions, lacerations, punctures and other categories of damage to layers of tissue, especially skin, each act to breach the protective tissue and blood vessels, allowing blood to flow out of its normal passageways. Bleeding provides a first line defense against damage from the ancillary effects of the trauma that caused the injury. The flow of blood washes material out of the wound and the blood clots to seal the wound area. The types of materials washed from the wound by the flow of blood from the traumatized area includes material introduced into the wound area by any foreign object which caused the wound (including biological species such as bacteria and viruses and inorganic species such as particulates). The clotting prevents migration of materials into the wound area, and therefore into the animals' body, thus reducing the likelihood of subsequent infection of the wound, even after materials originally introduced into the wound have been removed or reduced in volume by the initial blood flow.

Clotting is essential to both the short term and long term process of healing the wound. In the short term, after the wound has been partially cleansed by blood flow, the clotting entraps these removed materials so that they will not easily reenter the wound and stops the blood flow so that excessive blood loss will not occur. In the long term, the clot secures the wound minimizing additional tissue trauma (e.g., from flexing of the area) and preventing additional contaminants from entering the wound and blood stream.

Clotting is a complex biological process, driven by a series of cascading organic/biological chemical reactions which must occur in a specific sequence to cause the final effect of protecting the wound. In lay terms, the events in a simple wound where blood flow has occurred can be described as following a reaction path where a) Blood cells leak into a wound area; b) Blood vessels usually contract in the wound area to reduce the flow of blood; c) Platelets in the blood aggregate and adhere to tissue at the damaged site, even plugging small blood vessels; d) Platelets also interact with collagen, phospholipids, and tissue factor (a lipid-containing protein or lipoprotein, that stimulates blood clot formation); e) The platelets break-up and release thromboplastin, a poorly defined mixture of phospholipids and proteins that activate a series or cascade of reactions, usually catalyzed by serine proteases. The final product of these reactions is the enzyme thrombin which catalysis the conversion of the soluble blood protein, fibrinogen, to insoluble fibrin; f) The platelets provide nuclei upon which fibrin is bound to form the first stage of the moist clot, followed by subsequent maturation of the clot to form a firm coherent mass; g) Tissue forming cells, fibroblasts, approach the wound and associate with the moist clot to strengthen the region; h) The clot contracts and dehydrates, usually through evaporative processes, although there may be some absorption of liquid into the tissue; i) Phagocytes (white blood cells) move into the wound area to ingest microorganisms, cellular debris and any residual foreign matter; j) Epidermal cells at the edge of the wound divide and build a bridge across the wound.

The actual chemical and biological processes involved in the clotting process are quite complex and sophisticated. The process must be very selective, forming clots under only exacting conditions, so that clot formation does not occur in the circulatory system where clotting would itself be dangerous, causing phlebitis and certain types of strokes.

Wound management and clotting enhancement for wounds has taken many different paths over the years. There are a wide variety of different methodologies available for the management of wounds, depending, at least in part upon the type of wound and its severity. The two most common and effective treatments for minor bleeding wound management, following cleansing of the wound area, include direct application of pressure to the wound area and the topical application of an absorptive bandage to the wound surface. To assure the reduction of direct or secondary infections, all wound management should include cleansing and application of an antimicrobial agent to the wound area. After this cleansing step, the other methods may follow to control bleeding and prevent contamination of the wound. Direct application of pressure is usually effected by application of pressure manually or with a light wrapping. A sterile article is placed over the wound and pressure applied to the wound through the sterile article (e.g., a fabric, such as gauze, cotton ball, bandage, or other available, preferably sterilized or at least cleaned fabric). The pressure acts to assist in closing blood vessels in the area to reduce blood flow, absorb some of the initial blood flow with the highest content of foreign matter carried therein, and to stabilize the movement of the blood so that clotting is given time to initiate. The application of bandages to the wound area primarily acts to absorb excess blood, flow, provide a longer term barrier over the wound against introduction of foreign agents, protect the clot while it is still fragile (allowing it to dehydrate in the first twenty-four hours), and possibly carry and retain antimicrobial material to the wound surface.

The use of lasers, alone or in combination with topically applied patch materials (e.g., an elastin patch made from animal tissue), has been suggested for field treatment of bleeding wounds, both internal wounds and external or topical wounds. This has been specifically suggested as a field treatment, especially for the military, police, fire, and rescue services. Lasers by themselves can cauterize and seal vessel and organ wounds, and the patch can provide additional structural support for the area. http://detnews.com/96/discover/9701/05/12300058.htm.

Many folk remedies have also been applied as abrasion, but not open wound, treatments. For example, www://.drchristopher.com/ail/abrasio3.htm suggests the use of specific natural material treatments for abrasions where the skin has not been broken. The natural herbal agents include wheat grass chlorophyll, comfrey, healing ointment (comfrey, marshmallow, marigold, beeswax and oils), myrrh, plantain (and banana is also well known), and cayenne pepper. These materials may be applied directly to the abrasion area or carried on another surface, often with wetting suggested to retain the herbal abrasion treatment material. An Asian home remedy includes Dit Da Jao ("Iron Wine) which is a tincture remedy applied to relieve pain, stimulate blood flow and chi flow, and break up clots and bruises. The tincture is made up from powdered herbs and alcohol, with strained herbal residue discarded and the liquid tincture applied to the wound surface. The herbs to be used include *Arnica* blossom, comfrey, blessed thistle, goldenseal root, ginger root, Myrrh, sasparilla root, and witch hazel. Http://ww.aikidofaq.com/n.sub-section51.html)

Newer technology for wound management is the use of chemical bandages, or literally polymeric film-forming material over the wound area. This technology has passed from a fairly unsophisticated application of liquid glues (e.g., cyanoacrylate adhesives, gelatinous glues, and UV curable polymers) to the wound surface. In 1998, only the second liquid glue was granted FDA approval for use as stitches in addition to clotting enhancement, the glue apparently comprising a formaldehyde content cyanoacrylate. This glue is Closure Medical Corporation's DermaBond™, which is used as an alternative to Baxter HealthCare Corporation's Tisseel™, which is made from two blood proteins that naturally cause blood to clots. The cyanoacrylate must have a strong tendency for tissue irritation and carries a standard recommendation against use with patients with sensitivities to acrylates and formaldehyde, which are fairly common. HealthCare Corporation's Tisseel™, which is made from specific blood proteins thrombin and fibrinogen, is relatively expensive to manufacture. In addition, the use of human or animal derived protein compositions carries the risk of contamination by infectious agents such as hepatitis viruses, Human Immuno-Deficiency (HIV) viruses, or prions such as have been related to mad cow disease (bovine spongiform encephalitis) and Creutzfeld-Jakob disease. The Cryoseal™ clotting system uses cryoprecititated proteins obtained from the patients' blood as an adhesive. This fibrin glue adhesive is prepared and applied using a floor-standing, air-driven device in an operating theater.

U.S. Pat. No. 6,060,461 describes a method for enhancing the formation of clots on a wound of an animal where blood is present comprising the steps of applying porous particles with dimensions of from about 0.5 to 1000 micrometers to at least a portion of said wound where blood is present in said wound, allowing said porous particles to remain in contact with said blood in said wound while clotting initiates in said wound. The porous particles may have molecular sieve cutoff values between about 5,000 Daltons and 200,000 Daltons. The pores may comprise from 5 to 75% by volume of the porous particles.

PCT Application Publication WO 00/27327 describes a novel hemostatic composition comprising a substance containing uncharged organic hydroxyl groups and a substance containing at least one of a halogen atom and an epoxy group, which composition induces rapid blood coagulation and hemostasis at a wound or bleeding site. Examples of methods of application of the composition include, but are not limited to bags of materials, patches and bandaid-type patches, segments to be packed into cavities, fibers, fabrics, and the like.

It is known that fibrin clots are formed in vivo based upon the reaction of fibrinogen and thrombin in the presence of calcium ions. The initial phase of wound healing starts after the formation of fibrin clots, and involves the mobilization of cells from surrounding undamaged tissue. Normally, the earliest cells mobilized to the wound are inflammatory where they are active for a period of at least 1-3 days following injury. Subsequently, they are displaced by cells of the mesenchyme lineage which are immobilized into, navigate through and digest fibrin and replace fibrin with extracellular matrix (ECM) of different collagen types, fibronectin and hyaloron. Endothelial cells also infiltrate the fibrin and generate microcapillary structures. Ultimately, these cells replace the provisional fibrin matrix with granulation tissue populated by parenchymal cells and vasculature in secreted ECM.

Human fibroblasts are the major cellular entities responsible for the regeneration of the extracellular matrix (ECM) within the wound bed. Human fibroblasts also express specific membrane receptors to fibrinogen and thrombin. In the case of skin wounds, human fibroblasts reform the matrix of the dermis. For example, during the course of healing of an incisional skin wound, human fibroblasts are mobilized from the surrounding tissue and enter into the fibrin clots, help dissolve it and generate as well as reform the collagens (i.e., type I and type III) in the extracellular matrix. Based upon these properties of human fibroblasts, fibroblast implants have been suggested as a means for supplementing the body's natural wound healing regime (Gorodetsky, R., et al. Radiat. Res. 125:181-186 (1991)).

Benzoylated hyaluronic acid (HA) sheets containing holes or pores have been used as a carrier for fibroblasts and keratinocytes for wound healing (Andreassi, L., et al. Wounds 3(3): 116-126 (1991)). Specifically, HA sheets are cultured with these cells and then affixed to the site of the burn injury, where the cells migrate out of the sheet and accelerate the rate of wound regranulation. A major problem with implanted HA sheets, however, is that they are not metabolized by tissue, are cumbersome to administer, and may result in long-term immunological problems.

Purified fibrin(ogen) (which is known in the art as a mixture of fibrin and fibrinogen) and several of its lytic fragments (i.e., FPA, FPB, D and E) have been shown to be chemotactic to a variety of cells including macrophages, human fibroblasts (HF) and endothelial cells (Gorodetsky, R., et al. J. Lab. Clin. Med., in press (1997); Brown, L. F., et al. Amer. J. Pathol. 142:273-283 (1993); Clark, R. A. F., et al. J. Invest. Dermatol. 79:624-629 (1982); Ciano, P. S., et al. Lab. Invest. 54:62-69 (1986); Dejana, E., et al. J. Clin. Invest. 75:11-18 (1985)). Thrombin also has been shown to exert proliferative effect on various cells including fibroblasts, endothelial cells, and to enhance wound healing in rat skin (Kang, Y. H., et al. J. Histochem. Cytochem. 39:413-423 (1991); Shuman, F., NY Acad. Sci. 408:228-235 (1986); Biedermann, B., et al. J. Lab. Clin. Med. 124:339-347 (1994)).

Fibrin microbeads have been described in the prior art for use as drug delivery systems ((Ho, et al. Drug Dev. and Ind. Pharm. 20(4):535-546 (1994); Senderoff, et al. J. Parenteral Sci. & Tech. 45(1):2-6 (1991)). However, it has not been suggested or taught in the prior art that such fibrin microbeads have chemotactic and/or proliferative effects on any cells.

Furthermore, the fibrin microbeads of Ho, et al. and Senderoff, et al. would not be particularly useful or desirable as vehicles for culturing cells. In this regard, the Ho, et al. microbeads contain glutaraldehyde which cross-links proteins and destroys certain biologically active sites, thereby interfering with the binding of the microbeads to cells. Glutaraldehyde treatment may also render the microbeads immunogenic. The Senderoff, et al. microbeads contain essentially the same relatively low degree of cross-linking as fibrin. Thus, the Senderoff, et al. microbeads are not stable in aqueous solutions and therefore would not be useful as vehicles for culturing cells which require matrices that do not readily dissolve in aqueous solutions. U.S. Pat. No. 6,150,505 describes novel fibrin microbeads and their method of manufacture, where the fibrin microbeads are provided in the absence of glutaraldehyde.

One problem in the use of these medical or medicinal treatments is the application of the solids, particulates, fluid or otherwise flowable materials to the desired site. Sprinkling a material over the surface of a wound is effective, but can waste significant amounts of materials. It is desirable to be able to apply the materials more uniformly and specifically to a site. U.S. Pat. No. 6,241,697 shows a non-contact wound covering for covering a wound. A peripheral sealing ring is covered by a barrier layer and this assembly is attached to the skin with an adhesive. The barrier layer and peripheral sealing ring together define a treatment volume over the wound. The barrier layer may include active and passive heaters and the sealing ring may dispense water to control the humidity of the treatment volume. One form of active heat is the transfer of a heated fluid to the wound covering. In effect, an enclosed area is defined around a wound and liquid is directed into the enclosed area through a hose or tube.

U.S. Pat. No. 4,373,519 provides a system for removing liquids from a wound to promote healing, and embeds absorbent materials into a non-woven web that is applied to a surface. The non-woven web may be adhesively secured to the wound area.

U.S. Pat. No. 6,992,233 (Drake) describes a hemostatic starch delivery system including a delivery system for the delivery of flowable medicinal, therapeutic or medicine materials has a strip with flowable material contained and restrained therein. A removable seal is provided, so that when the removable seal is removed, the flowable material will flow from a storage area onto a site selected for treatment. The removable seal may be provided with additional features such as absorbent coatings, or additional disinfectants coatings useful in preparing the wound surface to receive the flowable wound treatment material. A preferred composition is a system, article, and method for the enhancement of clotting in wounds with extravascular blood flow, especially where the surface of the tissue has been broken.

US Patent Publication Nos. 20220241454 and 20220387659 (Lang) discloses a hemostatic surface application device having a region of hemostatic foam for contact with a patient's skin where a wound exists or is created, the device includes: a release layer, the release layer in contact with a hemostatic flexible foam section, and a structural foam layer having a front side and a back side surrounding the hemostatic flexible foam layer, forming a generally central hemostatic surface exposed through the front side of the surrounding structural foam layer, and a support layer adhered to the backside of the structural foam layer.

Clot formation can be needed in many different environments and individual structures and improved or optimized compositions can be needed for each particular field of use. All documents cited in this text are incorporated by reference in their entireties.

SUMMARY OF THE INVENTION

A device, and method for using that device, for carrying then delivering a sterile hemostasis material to a traumatic wound comprising:
a packet comprising a non-porous surface with an indented (e.g., recessed) area therein and a surrounding edge structure defining a perimeter around the indented area;
within the indented (e.g., recessed) area is a sterile hemostatic mass capable of clotting mammalian blood when the sterile hemostatic mass contacts mammalian blood;
a bottom layer of non-porous film attached to the surrounding edge structure to secure the sterile hemostatic mass within the packet, said bottom layer having a first end and a second end; and
a further lower layer below the bottom layer, away from the sterile hemostatic mass, and adhered to at least the first end of the bottom layer such that when the further lower layer is progressively manually pulled parallel to the surrounding edge structure, the at least second end of the bottom layer is progressively separated from the surrounding edge structure so that the sterile hemostatic mass is exposed.

BRIEF DESCRIPTION OF THE FIGURES

FIG. 1 is a perspective view of a ready-to-use sterile applicator for applying hemostatic material to a wound.

FIG. 2 is a side view of the ready-to-use sterile applicator of FIG. 1 for applying hemostatic material to a wound.

FIG. 2A is a bottom view of the ready-to-use sterile applicator of FIG. 1 for applying hemostatic material to a wound.

FIG. 3A shows a view of the ready-to-use sterile applicator of FIG. 1 applied to a wound.

FIG. 3B shows a view of the ready-to-use sterile applicator of FIG. 1 applied to a wound, with application of hemostatic agent initiated according to FIG. 4.

FIG. 4 shows a perspective view of the ready-to-use sterile applicator of FIG. 1 applied to a wound, with application of hemostatic agent initiated.

FIG. 4A shows a side view of the ready-to-use sterile applicator of FIG. 4 applied to a wound, with application of hemostatic agent initiated.

FIG. 4B shows a bottom view of the ready-to-use sterile applicator of FIG. 4 applied to a wound, with application of hemostatic agent initiated.

FIG. 5 shows a perspective view of the ready-to-use sterile applicator of FIG. 1 applied to a wound, with application of hemostatic agent initiated at a second stage.

FIG. 5A shows a side view of the ready-to-use sterile applicator of FIG. 5 applied to a wound, with application of hemostatic agent initiated at a second stage.

FIG. 5B shows a bottom view of the ready-to-use sterile applicator of FIG. 5 applied to a wound, with application of hemostatic agent initiated at a second stage.

FIG. 6 shows a perspective view of the ready-to-use sterile applicator of FIG. 1 applied to a wound, with application of hemostatic agent initiated at a third stage.

FIG. 6A shows a side view of the ready-to-use sterile applicator of FIG. 6 applied to a wound, with application of hemostatic agent initiated at a third stage.

FIG. 6B shows a bottom view of the ready-to-use sterile applicator of FIG. 6 applied to a wound, with application of hemostatic agent initiated at a third stage.

FIG. 7 shows a perspective view of the ready-to-use sterile applicator of FIG. 1 applied to a wound, with application of hemostatic agent initiated at a final stage, fully exposing the hemostatic agent.

FIG. 7A shows a side view of the ready-to-use sterile applicator of FIG. 7 applied to a wound, with application of hemostatic agent initiated at a final stage, fully exposing the hemostatic agent.

FIG. 7B shows a bottom view of the ready-to-use sterile applicator of FIG. 6 applied to a wound, with application of hemostatic agent initiated at a final stage, fully exposing the hemostatic agent.

DETAILED DESCRIPTION OF THE INVENTION

Figure 3:
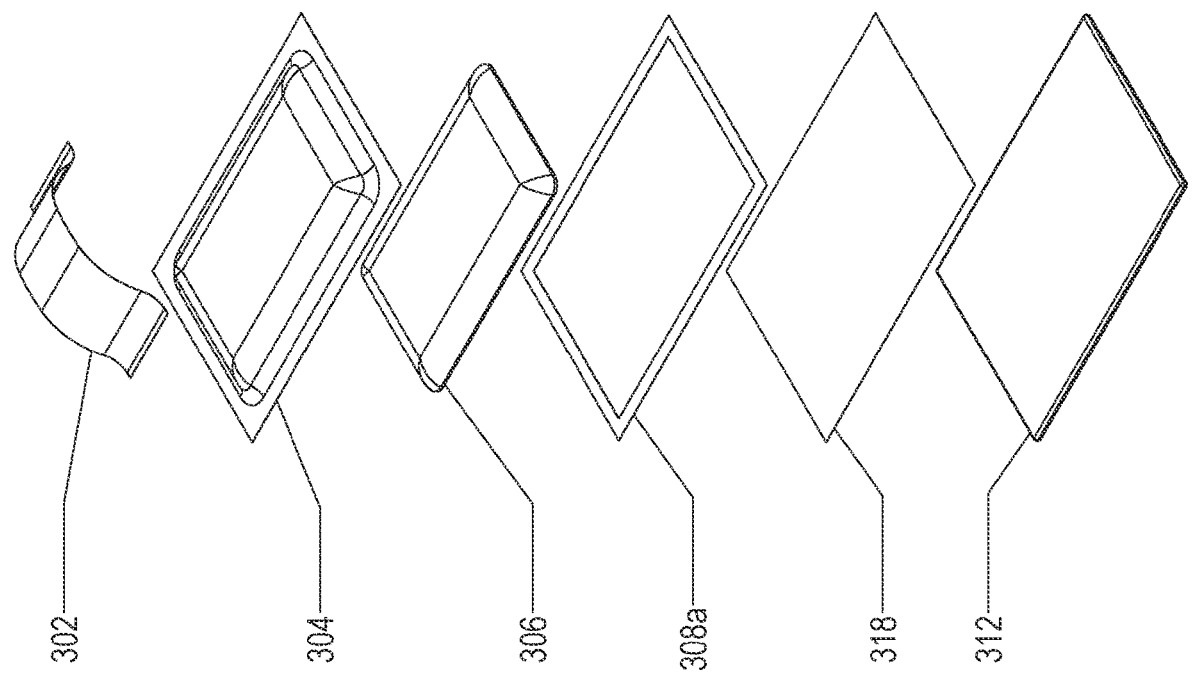
FIG. 3 shows a perspective exploded view of the ready-to-use sterile applicator of FIG. 1.

A device for carrying then delivering a sterile hemostasis material to a traumatic wound according to some of the practices of the present invention may include:
- a packet comprising a non-porous surface with an indented area therein and a surrounding edge structure defining a perimeter around the indented area, said packet having a leading edge and a rearward edge;
- within the indented area is a sterile hemostatic mass capable of clotting mammalian blood when the sterile hemostatic mass contacts mammalian blood;
- a bottom layer of non-porous film attached to the surrounding edge structure to secure the sterile hemostatic mass within the packet, said bottom layer having a first end and a second end corresponding respectively to the leading edge and the rearward edge of the packet; and
- a lower structural element below the bottom layer, away from the sterile hemostatic mass, and adhered to at least the first end of the bottom layer such that when the lower structural element is progressively manually pulled parallel to the surrounding edge structure, the at least first end of the bottom layer is progressively separated from the surrounding edge structure so that the sterile hemostatic mass is exposed.

The top surface of the packet may have a handle attached thereto.

The device may have a tacky adhesive (e.g., a low-to-medium tack, repositionable tack, or strippable tack) used to adhere the packet to the bottom layer to secure the sterile hemostatic mass within the packet. A tacky adhesive may be used as a coating, film, insert or the like to adhere the packet to the bottom layer to secure the sterile hemostatic mass within the packet. The lower structural element may be selected from the group consisting of an aqueous absorbent layer, a film, a pad, a pull-tape, and a string, the lower structural element being adhered to at least the first end of the bottom layer with sufficient force that the structural element will not tear as the first end of the bottom layer is progressively separated from the surrounding edge structure.

A device for carrying then delivering a sterile hemostasis material to a traumatic wound may include:
- a packet comprising a non-porous surface with an indented area therein and a surrounding edge structure defining a perimeter around the indented area;
- within the indented area is a sterile hemostatic mass capable of clotting mammalian blood when the sterile hemostatic mass contacts mammalian blood;
- a bottom layer of non-porous film attached by a tacky adhesive to the surrounding edge structure to secure the sterile hemostatic mass within the packet, said bottom layer having a first end and a second end; and
- a lower structural element comprising an aqueous absorbent pad below the bottom layer, away from the sterile hemostatic mass, and adhered to at least the first end of the bottom layer such that when the aqueous absorbent pad is progressively manually pulled parallel to the surrounding edge structure, the at least second end of the bottom layer is progressively separated from the surrounding edge structure so that the sterile hemostatic mass is exposed.

A method of treating a traumatic wound from which blood of a mammal is being exposed on tissue may include steps using the devices of the invention as described herein, wherein an operator/medical staff manipulates the devices by:
- contacting the leading edge of the packet adjacent a side of the wound;
- progressively pulling the lower structural element away from the leading edge of the packet to separate the at least first end of the bottom layer from the packet to expose sterile hemostatic mass to the traumatic wound.

The method may use a packet that has a handle thereon, and the handle is used to position the device for contact with the wound and to apply pressure to the device as the lower structural element is pulled. The pressure is generally or preferentially applied on a side of the packet opposite from the direction wherein the lower structural element is being withdrawn towards. Again, the method may be practiced wherein the lower structural element comprises an aqueous absorbent sheet which absorbs blood from the traumatic wound before or during the pulling of the lower structural element.

The method is preferably executed wherein the lower structural element comprises an aqueous absorbent sheet which absorbs blood from the traumatic wound before or during the pulling of the lower structural element. The pad may be wiped across the upper surface of the wound. In the execution of the method, the bottom layer may retract and fold over itself as the lower structural element is pulled.

Although the device of the present invention may be used on any wound where blood flow desires clotting in the wound area, the present invention is especially useful where there is significant tissue damage and moderate to heavy bleeding, and immediate or rapid clotting is medically necessitated. For example, wounds from weapons, shrapnel, glass, mechanical equipment (e.g., saws, blades, belts, machinery, etc.), falling objects and other military injuries or first respondent accidents require such urgent and immediate care to improve survival rates.

FIG. 1 is a perspective view of a ready-to-use sterile applicator 100 for applying hemostatic material to a wound. The sterile applicator 100 is shown with a handle 302, a pouch 304 (for retaining hemostatic mass, not shown), and a removeable base 312.

FIG. 2 is a side view of the ready-to-use sterile applicator 100 of FIG. 1 for applying hemostatic material to a wound. The handle 302 and the removable base 312 are shown.

FIG. 2A is a bottom view of the ready-to-use sterile applicator of FIG. 1 for applying hemostatic material to a wound. Only the removeable base 212 is seen from this perspective.

FIG. 3 shows an exploded perspective view of the ready-to-use sterile applicator 100 of FIG. 1. From top to bottom are shown a handle 302 positioned at the top of the sterile applicator to allow ease of manual application and applied pressure on the sterile application. It may be made of plastic, composite, cellulosic materials, metal, ceramic or any other structural material. The handle 302 is attached to a top surface of the pouch 304, which again, may be made of plastic, composite, cellulosic materials, metal, ceramic or any other structural material. Within the pouch 304 is nestled sterile hemostatic material 306 which is used to stop the bleeding from a traumatic wound. The hemostatic material 306 may be a powder, a foam, a sheet, a fabric, a fabrication, compressed mass or other form which can consist of, comprise or carry the hemostatic material. Any hemostatic material may be used, but a more thorough description of preferred materials is provided within this disclosure.

An optional but preferred layer 308a of a low tack adhesive edging (it need not be a complete sheet, but rather a coated layer, a coated edge, a skeletal frame, etc.) to secure the pouch or top layer 304 to lower layers/elements below the hemostatic material 306. A bottom (release layer) 318 is secured to the pouch/top layer 304 either directly (without the optional low tack adhesive layer 308a) or with the adhesive layer 308a. The bottom layer 318 (of plastic, paper, coated paper, foil, etc.) is to be removed/peeled off the pouch 304 or the optional adhesive layer 308a, allowing the hemostatic material 306 to contact the wound.

A bottom, removeable base 312 is shown. This layer is typically a sheet or film, and may even be an absorbent pad of foam, composite, film or fabric attached at one end of the bottom layer 318 to wipe away/absorb excess blood while pulling the bottom layer away to expose the hemostatic material 306.

FIG. 3A shows a view of the ready-to-use sterile applicator 100 of FIG. 1 applied to a wound on flesh 330.

FIG. 3B shows a view of the ready-to-use sterile applicator 100 of FIG. 1 applied to a wound, with application of hemostatic agent initiated according to FIG. 4 by removal of the removeable base 312.

FIG. 4 shows a perspective of the ready-to-use sterile applicator 100 of FIG. 1. The handle 302 and pouch 304 are shown as the removeable base 312 is pulled away from the pouch 304.

FIG. 4A shows a side view of the ready-to-use sterile applicator 100 of FIG. 1. The handle 302 and pouch 304 are shown as the removeable base 312 is pulled away from a flat extension 308 of the pouch of the sterile applicator 100. The flat extension 308 of the pouch 304 may be adhesive to secure the opened pouch 304 with its restrained/contained hemostatic mass/sheet/material (not shown) against the wound (not shown). A release layer 318 is being removed from the pouch 304 as the removeable base 312 is pulled. The removeable base 312 is attached to the release layer at a rollover point 314. As the removeable base 312 is withdrawn away from the flat extension 308, the rollover point 314 continues to be moved, pulling more of the release layer 318 with it. During application of tension to the removeable base 312 the application of force along vector 316 assists in maintaining contact of the flat extension 308 with areas around the wound (not shown).

FIG. 4B shows a bottom view of the ready-to-use sterile applicator 100 of FIG. 4 applied to a wound (not shown), with application of hemostatic agent 306 initiated as it is exposed from within the pouch 304. The coincident withdrawal of the release layer 318 is shown as it is pulled along with the removeable base 312 to expose the hemostatic material 306 which ultimately is put into contact with the wound (not shown).

FIG. 5 shows a perspective view of the ready-to-use sterile applicator 100 of FIG. 1 applied to a wound, with application of hemostatic agent initiated at a second stage in which the removeable base 312 is further extended away from the pouch 304 and handle 302. The release layer 318 is also further withdrawn.

FIG. 5A shows a side view of the ready-to-use sterile applicator 100 of FIG. 1 applied to a wound, with application of hemostatic agent initiated at a third stage. The handle 302 and pouch 304 are shown as the removeable base 312 is pulled away from a flat extension 308 of the pouch of the sterile applicator 100. The flat extension 308 of the pouch 304 may be adhesive to secure the opened pouch 304 with its restrained/contained hemostatic mass/sheet/material 306 against the wound (not shown). A release layer 318 is being removed from pouch 304 as the removeable base 312 is pulled. The removeable base 312 is attached to the release layer at a rollover point 314. As the removeable base 312 is withdrawn away from the flat extension 308, the rollover point 314 continues to be moved, pulling more of the release layer 318 with it. During application of tension to the removeable base 312 the application of force along vector 316 assists in maintaining contact of the flat extension 308 with areas around the wound (not shown).

FIG. 5B shows a bottom view of the ready-to-use sterile applicator 100 of FIG. 5 applied to a wound, with application of hemostatic agent 306 from the pouch 304 initiated at a third stage. All numbered elements with identical numbering represent same elements in all figures, although the state of those elements may vary.

FIG. 6 shows a perspective view of the ready-to-use sterile applicator 100 of FIG. 1 applied to a wound, with application of hemostatic agent (not shown) initiated at a fourth stage.

FIG. 6A shows a side view of the ready-to-use sterile applicator 100 of FIG. 1 applied to a wound, with application of hemostatic agent 306 initiated at a fourth stage.

FIG. 6B shows a bottom view of the ready-to-use sterile applicator 100 of FIG. 6 applied to a wound, with application of hemostatic agent 306 initiated at a fourth stage.

FIG. 7 shows a perspective view of the ready-to-use sterile applicator 100 of FIG. 1 applied to a wound by handle 302, with application of hemostatic agent (not shown, under packet 304) initiated at a final stage, fully exposing the hemostatic agent 306.

FIG. 7A shows a side view of the ready-to-use sterile applicator 100 of FIG. 1 applied to a wound, with application of hemostatic agent 702 initiated at a final stage, fully exposing the hemostatic agent 306. In the Figures, optional element 310 (in FIG. 7B) is a band of adhesive strip that may surround a self-supporting hemostatic material and secure it over a wound after release of the hemostatic mass from the pouch 304.

FIG. 7B shows a bottom view of the ready-to-use sterile applicator 100 of FIG. 1 applied to a wound, with application of hemostatic agent 306 initiated at a final stage, fully exposing the hemostatic agent 306. The removeable base 312 and the release layer 318 are fully extended and may be removed, leaving the hemostatic material 306 in place over the wound. An optional element 310 is a band of adhesive strip that may surround a self-supporting hemostatic material and secure it over a wound after release of the hemostatic mass from the pouch 304.

The hemostatic agent may include any of the wide array of hemostatic agents known in the medical field, including Iron Sulfates, Aluminum Sulfates, starch, chitosan, microporous particles, powders, films and foams. A preferred foam may be described as a material having a region of hemostatic foam for contact with a patient's skin where a wound exists or is created. A structural foam layer may have a front side and a back side surrounding the hemostatic flexible foam layer. The surrounding structure of the structural foam forms a generally central hemostatic surface (of the hemostatic foam) exposed through the front side of the surrounding structural foam layer. It may desirable that a support layer is adhered to the back side of the structural foam layer, away from the surface applied to a traumatic wound. The hemostatic flexible foam layer should be able to retain at least 99.5% of total weight of the hemostatic flexible foam layer when in contact with a surface having a 5 micron thick layer of water on its surface for 1 minute. The hemostatic flexible foam layer may include a polysaccharide foam composition. The hemostatic flexible foam layer may include a polysaccharide foam composition. The device may have the hemostatic flexible foam layer with a thickness at least 1% greater than the thickness of the structural foam layer. The structural foam layer may a polyurethane foam, either closed cell, open-cell or the like. Other foams may be used (as the foam has not chemical requirements except to be non-irritating to skin, and performs only a structural effect), such as polysiloxane foams, polycellulosic foams, and other polymeric foams. The device may have the support layer adhered to the backside of the structural foam layer by an adhesive layer.

A method of reducing excessive blood flow off an exterior surface wound of a patient comprising removing the bottom layer and lower layer sterile hemostatic mass application device as described above, and applying the generally central hemostatic foam layer (or other contained hemostatic mass as liquid, powder, film, etc.) to a limited area of skin of the patient. The method may be executed wherein, after applying the generally central hemostatic foam layer (or sterile hemostatic mass) to a limited area of skin of the patient, a catheter or needle is inserted through the hemostatic foam layer of the hemostatic surface application device and into the skin of the patient. In this process, after inserting the catheter or needle through the skin of the patient, blood exudes from the skin of the patient and is clotted by the hemostatic foam layer. Furthermore, in this method, the hemostatic flexible foam layer retains at least 99.5% of total weight of the hemostatic flexible foam layer when in contact with blood exuding from the skin of the patient for 1 minute.

Hemostatic foam compositions are known in the medical field, but they have had limited numbers of variations in structural forms within the field. Among known foams that can be used within the practice of the present invention are those shown by the following background art.

US Published Patent Application Document 2015/0314037 and 2014/0161738 (Andreas) discloses a pharmaceutical hemostatic liquid foam base preparation comprising albumin as foaming agent and a fibrinogen precipitating substance and optionally a coagulation inducing agent, wherein albumin as foaming agent is present in native form; a method for the production of a transient hemostatic liquid foam; the transient hemostatic liquid foam; and a kit for making the foam.

US Published Patent Application Documents 2017/0136054 and 2014/0010887 and 2009/0062233 (Ji) evidences a modified starch material for biocompatible hemostasis, biocompatible adhesion prevention, tissue healing promotion, absorbable surgical wound sealing and tissue bonding, when applied as a biocompatible modified starch to the tissue of animals. The modified starch material, which may be in the form of a foam, produces hemostasis, reduces bleeding of the wound, extravasation of blood and tissue exudation, preserves the wound surface or the wound in relative wetness or dryness, inhibits the growth of bacteria and inflammatory response, minimizes tissue inflammation, and relieves patient pain. The hemostatic materials, which may be in foam form, can be provided by adding the functional group on the raw starch glucose units with chemical agents, e.g., by carboxylation modification, or hydroxylation modification, the starch captures hydrophilic groups in its molecular structure and obtains hydrophilic properties, By using bifunctional or polyfunctional chemical agents to cross-link the raw starch macromolecules or grafting external macromolecular hydrophilic groups to the raw starch, the starch acquires enhanced hydrophilic properties and viscosity/adhesiveness in a water solution. The viscosity of modified starch relates to the raw starch origin and the degree of substitution of external and cross-linked or grafted functional groups, etc. When contacting blood, the hydrophilic and adhesive properties of the modified starch of the present invention produce a "starch-blood coagulation matrix" with strong adhesive characteristics which can seal wounded tissue and stop bleeding. In addition, the interaction between the formed blood coagulation matrix and the functional groups of tissue proteins causes the "starch-blood coagulation matrix" to adhere to and seal the wounded tissue, resulting in hemostasis.

US Published Patent Application Document 2013/0096479 discloses a hemostatic product having a plurality of hemostatic layers. Each of the hemostatic layers includes a dextran support and at least one hemostatic agent, which is selected from the group consisting of thrombin and fibrinogen. The hemostatic layers are arranged in a stacked configuration. The thrombogenic agent may be applied onto open-cell or closed-cell foam supports.

US Published Patent Application Document 20120114592 (Zuidema) is directed to hemostatic foams and to the preparation of such foams. In a first aspect, the present invention provides a biodegradable hemostatic foam comprising a polymer blend of a water-soluble polymer and a phase-separated polyurethane comprising an amorphous segment and a crystalline segment, wherein at least said amorphous segment comprises a hydrophilic segment.

A device according to the present invention carries then delivers a sterile hemostasis material to a traumatic wound. The device may include:
  a packet comprising a non-porous surface with an indented area therein and a surrounding edge structure defining a perimeter around the indented area, said packet having a leading edge and a rearward edge;
  within the indented area is a sterile hemostatic mass capable of clotting mammalian blood when the sterile hemostatic mass contacts mammalian blood;
  a bottom layer of non-porous film attached to the surrounding edge structure to secure the sterile hemostatic mass within the packet, said bottom layer having a first end and a second end corresponding respectively to the leading edge and the rearward edge of the packet; and
  a lower structural element below the bottom layer, away from the sterile hemostatic mass, and adhered to at least the first end of the bottom layer such that when the lower structural element is progressively manually pulled parallel to the surrounding edge structure, the at least second end of the bottom layer is progressively separated from the surrounding edge structure so that the sterile hemostatic mass is exposed.

A top surface of the packet preferably has a handle attached thereto. A tacky adhesive (preferably low-to-medium tack, including pressure-sensitive, thermal and solvent applicable tacky adhesives) is used to adhere the packet to the bottom layer to secure the sterile hemostatic mass within the packet.

The lower structural element is selected from the group consisting of (porous or solid) an aqueous absorbent layer, a film, a pad, a sheet, fabric, a pull-tape, and a string, the lower structural element being adhered to at least the first end of the bottom layer with sufficient force that the structural element will not tear as the first end of the bottom layer is progressively separated from the surrounding edge structure.

A device for carrying then delivering a sterile hemostasis material to a traumatic wound comprising:
  a packet comprising a non-porous surface with an indented area therein and a surrounding edge structure defining a perimeter around the indented area;
  within the indented area is a sterile hemostatic mass capable of clotting mammalian blood when the sterile hemostatic mass contacts mammalian blood;
  a bottom layer of non-porous film attached by a tacky adhesive to the surrounding edge structure to secure the sterile hemostatic mass within the packet, said bottom layer having a first end and a second end; and
  a lower structural element comprising an aqueous absorbent pad below the bottom layer, away from the sterile hemostatic mass, and adhered to at least the first end of the bottom layer such that when the aqueous absorbent pad is progressively pulled parallel to the surrounding edge structure, the at least first end of the bottom layer is progressively separated from the surrounding edge structure so that the sterile hemostatic mass is exposed, wherein a top surface of the packet has a handle attached thereto.

A method of treating a traumatic wound from which blood of a mammal is being exposed on tissue, comprising:
  providing the device of claim 1 in proximity to the wound;
  contacting the leading edge of the packet adjacent a side of the wound;
  progressively pulling the lower structural element away from the leading edge of the packet to separate the at least first end of the bottom layer from the packet to expose sterile hemostatic mass to the traumatic wound.

In this method, the packet may have a handle thereon, and the handle is used to position the device for contact with the wound and to apply pressure to the device as the lower structural element is pulled.

Preferably in the method, the lower structural element comprises an aqueous absorbent sheet which absorbs blood from the traumatic wound before or during the pulling of the lower structural element.

The terms used herein have their common meanings within the field of practice, even though alternative terms may be used. For example, the "packet" may be a pouch, recessed volume, a cup, and the like. Additional structure, steps and materials may be added to the device and methods of the present invention without avoiding the scope of the present invention. For example, it environments where the packet is applied and additional physical stress may occur on the patient (e.g., in medical evacuation or other transportation or movement), tape may be applied over the device to further secure it to the patient. The case may also be removed after the sterile hemostatic mass has been applied to a wound (preferably with ongoing, active blood flow from the wound), and significant clotting has been initiated. Coverings may then be applied over the hemostatic mass.

What is claimed:

1. A device for carrying then delivering a sterile hemostasis material to a traumatic wound composing:
  a packet comprising a non-porous surface with a recessed area therein and a surrounding edge structure defining a perimeter around the recessed area, said packet having a leading edge and a rearward edge;
  within the recessed area is a sterile hemostatic mass capable of clotting mammalian blood when the sterile hemostatic mass contacts mammalian blood;
  a bottom layer of non-porous film is attached to the surrounding edge structure to secure the sterile hemostatic mass within the packet, said bottom layer having a first end and a second end corresponding respectively to the leading edge and the rearward edge of the packet; and
  a lower structural element below the bottom layer, away from the sterile hemostatic mass, and adhered to at least the second end of the bottom layer such that when the lower structural element is progressively pulled parallel to the surrounding edge structure, the second end of the bottom layer is progressively separated from the surrounding edge structure, exposing the sterile hemostatic mass, and
  wherein the lower structural element further comprises an aqueous absorbent sheet to absorb blood from the traumatic wound before or during the pulling of the lower structural element.

2. The device of claim 1 wherein a top surface of the packet has a handle attached thereto.

3. The device of claim 1 wherein a tacky adhesive is used to adhere the packet to the bottom layer to secure the sterile hemostatic mass within the packet.

4. The device of claim 2 wherein a tacky adhesive is used to adhere the packet to the bottom layer to secure the sterile hemostatic mass within the packet.

5. The device of claim 1 wherein the lower structural element is selected from the group consisting of an aqueous absorbent layer, a film, a pad, a pull-tape, and a string,
  the lower structural element being adhered to at least the second end of the bottom layer with sufficient force that the structural element will not tear as the second end of the bottom layer is progressively separated from the surrounding edge structure.

6. The device of claim 2 wherein the lower structural element is selected from the group consisting of an aqueous absorbent layer, a film, a pad, a pull-tape, and a string,
  the lower structural element being adhered to at least the second end of the bottom layer with sufficient force that the structural element will not tear as the second end of the bottom layer is progressively separated from the surrounding edge structure.

7. The device of claim 3 wherein the lower structural element is selected from the group consisting of an aqueous absorbent layer, a film, a pad, a pull-tape, and a string,
  the lower structural element being adhered to at least the second end of the bottom layer with sufficient force that the structural element will not tear as the second end of the bottom layer is progressively separated from the surrounding edge structure.

8. The device of claim 4 wherein the lower structural element is selected from the group consisting of an aqueous absorbent layer, a film, a pad, a pull-tape, and a string,
  the lower structural element being adhered to at least the second end of the bottom layer with sufficient force that the structural element will not tear as the second end of the bottom layer is progressively separated from the surrounding edge structure.

9. A device for carrying then delivering a sterile hemostasis material to a traumatic wound comprising:
  a packet comprising a non-porous surface with an indented area therein and a surrounding edge structure defining a perimeter around the indented area;
  within the indented area is a sterile hemostatic mass capable of clotting mammalian blood when the sterile hemostatic mass contacts mammalian blood;
  a bottom layer of non-porous film attached by a tacky adhesive to the surrounding edge structure to secure the sterile hemostatic mass within the packet, said bottom layer having a first end and a second end; and a lower structural element comprising an aqueous absorbent pad below the bottom layer and away from the sterile hemostatic mass, and the lower structural element is adhered to at least the second end of the bottom layer such that when the aqueous absorbent pad is progressively manually pulled parallel to the surrounding edge structure, the second end of the bottom layer is progressively separated from the surrounding edge structure so that the sterile hemostatic mass is exposed, and wherein the lower structural element further comprises an aqueous absorbent sheet to absorb blood from the traumatic wound before or during the pulling of the lower structural element.

10. The device of claim 9 wherein a top surface of the packet has a handle attached thereto.

11. A method of treating a traumatic wound from which blood of a mammal is being exposed on tissue, comprising:
providing a device for carrying then delivering a sterile hemostasis material to a traumatic wound, the device comprising:
a packet comprising a non-porous surface with a recessed area therein and a surrounding edge structure defining a perimeter around the recessed area, said packet having a leading edge and a rearward edge;
within the recessed area is a sterile hemostatic mass capable of clotting mammalian blood when the sterile hemostatic mass contacts mammalian blood;
a bottom layer of non-porous film is attached to the surrounding edge structure to secure the sterile hemostatic mass within the packet, said bottom layer having a first end and a second end corresponding respectively to the leading edge and the rearward edge of the packet; and
a lower structural element below the bottom layer, away from the sterile hemostatic mass, and adhered to at least the second end of the bottom layer such that when the lower structural element is progressively pulled parallel to the surrounding edge structure, the second end of the bottom layer is progressively separated from the surrounding edge structure, exposing the sterile hemostatic mass in proximity to the wound;

contacting the leading edge of the packet adjacent a side of the wound;

progressively pulling the lower structural element away from the leading edge of the packet to separate at least the second end of the bottom layer from the packet to expose sterile hemostatic mass to the traumatic wound, and further wherein the lower structural element comprises an aqueous absorbent sheet which absorbs blood from the traumatic wound before or during the pulling of the lower structural element.

12. The method of claim 11 wherein the packet has a handle thereon, and the handle is used to position the device for contact with the wound and to apply pressure to the device as the lower structural element is pulled.

13. The method of claim 12 wherein the bottom layer retracts and folds over itself as the lower structural element is pulled.

14. The method of claim 11 wherein the lower structural element comprises an aqueous absorbent sheet which absorbs blood from the traumatic wound during the pulling of the lower structural element.

15. The method of claim 12 wherein the lower structural element comprises an aqueous absorbent sheet which absorbs blood from the traumatic wound during the pulling of the lower structural element.

16. The method of claim 13 wherein the lower structural element comprises an aqueous absorbent sheet which absorbs blood from the traumatic wound during the pulling of the lower structural element.

17. The device of claim 1 wherein the lower structural element comprises an aqueous absorbent sheet which absorbs blood from the traumatic wound during the pulling of the lower structural element.

18. The device of claim 9 wherein the lower structural element comprises an aqueous absorbent sheet which absorbs blood from the traumatic wound during the pulling of the lower structural element.

19. The device of claim 10 wherein the lower structural element comprises an aqueous absorbent sheet which absorbs blood from the traumatic wound during the pulling of the lower structural element.

* * * * *